United States Patent [19]

Mouzin et al.

[11] 4,380,667
[45] Apr. 19, 1983

[54] 2'-(ORTHOCHLOROBENZOYL)-4'-CHLOROGLYCYLANILIDES, COMPOSITIONS THEREOF, AND USE AS MEDICAMENTS

[75] Inventors: Gilbert Mouzin; Henri Cousse; Antoine Stenger, all of Castres, France

[73] Assignee: Pierre Fabre S.A., Paris, France

[21] Appl. No.: 76,841

[22] Filed: Sep. 19, 1979

[30] Foreign Application Priority Data

Sep. 25, 1978 [FR] France .................. 78 27401

[51] Int. Cl.$^3$ .................................. C07C 103/50
[52] U.S. Cl. .................. 564/195; 564/188; 564/189; 564/190; 564/191; 424/324; 424/315; 424/316; 260/501.17
[58] Field of Search .......... 260/557 R, 562 N, 501.17; 564/188, 189, 190, 191, 195

[56] References Cited

U.S. PATENT DOCUMENTS

| | | | |
|---|---|---|---|
| 3,202,699 | 8/1965 | Stempel | 260/562 N X |
| 3,429,874 | 2/1969 | Topliss | 260/562 N X |
| 3,547,993 | 12/1970 | Bell | 260/562 N X |
| 3,914,215 | 10/1975 | Tachikawa et al. | 260/562 N X |
| 4,075,409 | 2/1978 | Greve et al. | 260/562 N X |

FOREIGN PATENT DOCUMENTS 253816  5/1963  Australia .................. 260/562 N

Primary Examiner—Thomas A. Waltz
Attorney, Agent, or Firm—Gordon W. Hueschen

[57] ABSTRACT

The present invention relates to 2'-(ortho-chlorobenzoyl)-4'-chloroglycylanilides, compositions thereof, and their use as medicaments, e.g., as anxiolytic agents.

The compounds of the invention have the general formula I

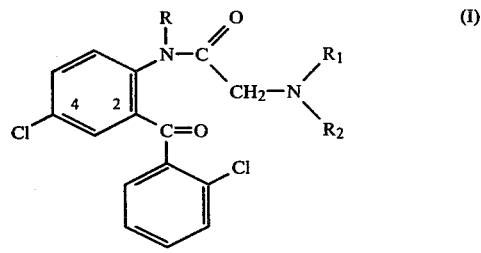

in which
R represents hydrogen or alkyl,
$R_1$ and $R_2$ may be identical or different and are selected from hydrogen, alkyl, hydroxyalkyl, alkenyl, and alkynyl, possibly substituted by alkyl, and cycloalkyl having three to six members, possibly substituted by alkyl, with the proviso that, when one of $R_1$ and $R_2$ represents hydrogen, the other is not lower alkyl or hydroxyalkyl; and with the further proviso that $R_1$ and $R_2$ may not simultaneously represent either hydrogen or lower alkyl. $R_1$ and $R_2$ may furthermore form, with the nitrogen atom to which they are connected, a nitrogen heterocycle possibly containing a second heteroatom selected from oxygen and nitrogen.

3 Claims, No Drawings

2'-(ORTHOCHLOROBENZOYL)-4'-CHLOROGLYCYLANILIDES, COMPOSITIONS THEREOF, AND USE AS MEDICAMENTS

FIELD OF INVENTION

Specifically substituted 2'-(ortho-chlorobenzoyl)-4'-chloroglycylanilides; anxiolytic agents; pharmaceutical compositions thereof; method of treating therewith.

OBJECTS OF INVENTION

It is an object of the invention to provide novel 2'-(ortho-chlorobenzoyl)-4'-chloroglycylanilides, including acid addition salts thereof, which are useful as medicaments and particularly useful as anxiolytic agents; pharmaceutical compositions thereof in association with a pharmaceutically acceptable carrier, diluent, or excipient, and a method of treating a patient suffering from anxiety or an anxious state by administering to the patient a compound of the invention in an amount effective for alleviation of such condition. Other objects will become apparent hereinafter and still others will be obvious to one skilled in the art.

SUMMARY OF THE INVENTION

The present invention relates to novel derivatives of 2'-(ortho-chlorobenzoyl)-4'-chloroglycylanilides, their method of preparation, pharmaceutical compositions thereof, and their use as medicaments, e.g., as anxiolytic agents.

The new compounds of the present invention have the general formula I:

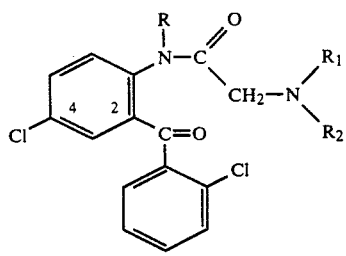

in which:
R represents hydrogen or alkyl, preferably methyl;
$R_1$ and $R_2$ may be identical or different and are selected from hydrogen, alkyl, hydroxyalkyl, alkenyl and alkynyl, optionally substituted one or more times by alkyl; and cycloalkyl having three to six ring carbon atoms and optionally substituted by alkyl, provided that, when one of $R_1$ and $R_2$ represents hydrogen, the other is not lower-alkyl or hydroxyalkyl; and provided further that $R_1$ and $R_2$ cannot simultaneously represent either lower-alkyl or hydrogen.
$R_1$ and $R_2$ may furthermore form, with the nitrogen atom to which they are connected, a nitro heterocycle possibly containing a second heteroatom selected from oxygen and nitrogen.

An illustrative explanation of certain meanings given with respect to the radicals R, $R_1$ and $R_2$ will now be indicated. First, they contain up to and including eight (8) carbon atoms in any event and, where lower-alkyl, lower-alkenyl, or lower-alkynyl, preferably five (5) carbon atoms or less. The alkyl groups may be straight or branched-chain alkyl such as methyl, ethyl, propyl, isopropyl, butyl, isobutyl, sec.butyl, tert.butyl, pentyl, isopentyl, neopentyl, tert.pentyl, hexyl, isohexyl, heptyl, and octyl. "Cycloalkyl" preferably has three to six ring carbon atoms, such as cyclopropyl, cyclobutyl, cyclopentyl, methyl or propyl cyclopentyl, and cyclohexyl. Alkenyl groups may representatively be allyl, butenyl, pentadienyl, or the like. Alkynyl groups may representatively be ethynyl, propargyl, or the like. Finally, the saturated or unsaturated heterocycles are selected, for instance, from among the pyrrolyl, imidazolyl, pyrazolyl, isoxazolyl, pyridyl, pyrazinyl, pyrimidinyl, pyridazinyl, pyrrolidinyl, imidazolidinyl, pyrazolidinyl, piperidyl, piperazinyl, and morpholinyl groups, and the like. Hydroxyalkyl is alkyl with one or more hydroxy groups therein, at least one of which is preferably an omega-hydroxy group, such as omega-hydroxyethyl, propyl, butyl, and amyl, 3-hydroxybutyl, 3,4-hydroxyamyl, and the like. The present invention especially concerns compounds of formula I in which the radical R represents lower-alkyl, and particularly methyl.

The present invention applies also to pharmaceutically-acceptable acid addition salts of a compound of formula I with the usual therapeutically-acceptable acids. By way of non-limitative examples of therapeutically or physiologically-acceptable addition salts, mention may be made of the salts of inorganic acids such as hydrochloric, phosphoric and sulfuric acids, and the salts of organic acids such as maleic, succinic, fumaric, citric, and the like.

The present invention also concerns a process of preparing compounds of formula I characterized by condensing a compound of general formula II:

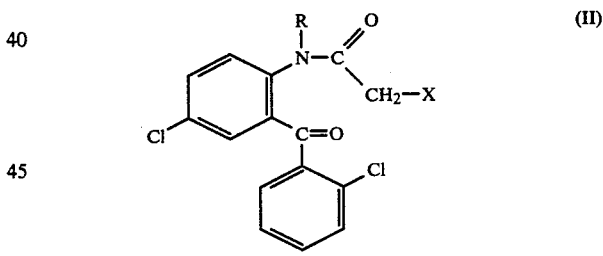

in which: R has the meaning given in connection with formula I and X represents a replaceable halogen atom, with an amine of formula III:

in which $R_1$ and $R_2$ have the meanings given in connection with general formula I. The starting materials of general formula II can be prepared from aminobenzophenones obtained by the method of L. H. STERNBACH and R. Ian FRYER - J. Org. Chem. 27, 3781, 1962, or in accordance with the process of French Pat. No. 78 26918, in accordance with the following reaction sequence:

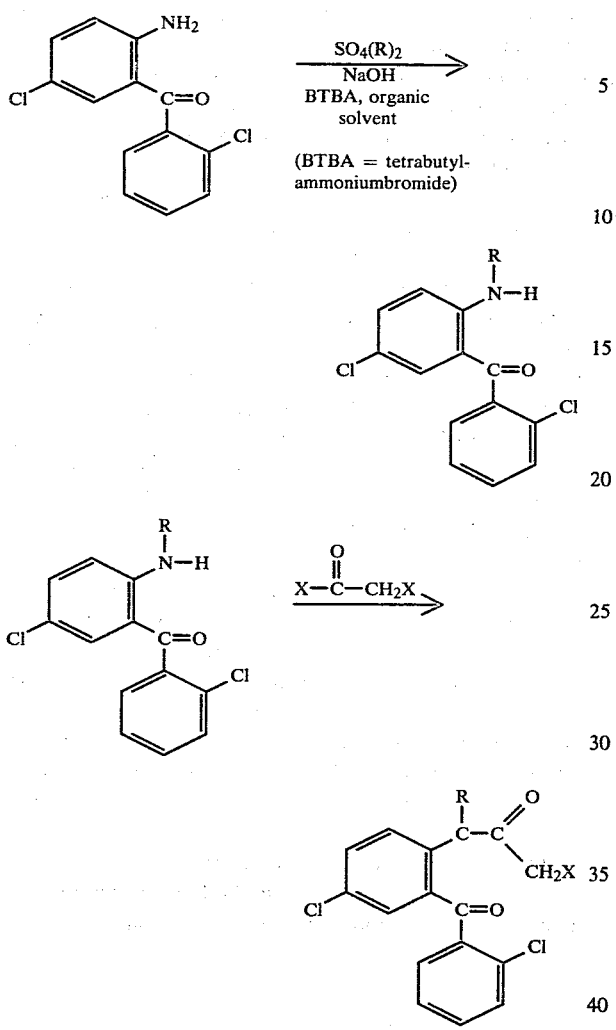

wherein X represents a replaceable halogen atom, e.g., bromine or chlorine, and R has the meaning given previously. From the foregoing, it is apparent that to vary the alkyl group of R and $R_1$ in final product of formula I, it is only necessary to vary the alkyl group R of the starting material of formula II, or to vary the alkyl group $R_1$ of the starting material of formula III, or both, all according to the foregoing reaction sequence. Similarly, variation of the cyclic group or groups $R_1$ $R_2$ is effectively accomplished merely by variation of these groups in the starting material of formula III.

The present invention also concerns the use of the compounds of general formula I as medicaments which act on the central nervous system and, in particular, as anxiolytic agents, as well as sedative, anticonvulsive, and hypnotic agents, and as muscle relaxants, and pharmaceutical compositions thereof containing the active ingredient plus the usual pharmaceutically-acceptable carrier, diluent, or excipient.

DETAILED DESCRIPTION OF INVENTION

The present invention will be described in further detail hereinafter on a basis of the following examples, which are given by way of illustration only and are not to be construed as limiting.

EXAMPLE 1

N-methyl-N-(2-hydroxyethyl)2'-(ortho-chlorobenzoyl)-4'-chloroglycylanilide (a) Preparation of 2-bromacetamido-2',5-dichlorobenzophenone To an iced solution of 266 g (1 mol) of 2-amino-2',5-dichlorobenzophenone in 3 liters of ethyl ether there are added, drop by drop, 90 cc (1.1 mol) of bromacetyl chloride dissolved in 500 cc of ethyl ether. The batch is allowed to come to room temperature, whereupon it is evaporated to dryness and the crystalline residue extracted with petroleum ether and filtered. In this manner, 371 g of crystals are recovered.

Yield: 96%
Melting point: 136°–137° C.
Plate chromatography:
support: Silica gel 60 F 254 Merck
solvent: ethyl acetate/petroleum ether 30/70
development: UV and iodine
Rf: 0.82

(b) Preparation of N-methyl-N-(2-hydroxyethyl)-2'-(ortho-chlorobenzoyl)-4'-chloroglycylanilide To a suspension of 139.3 g (0.36 mol) of 2-bromoacetamido-2',5-dichlorobenzophenone and 2 liters of acetone there are added 60 cc (0.76 mol) of 2-methylaminoethanol followed by heating for 15 hours under reflux. The reaction solvent is then evaporated to dryness and the crystalline residue absorbed with isopropyl ether and extracted with a 1 N hydrochloric acid solution. The aqueous phase is treated with sodium bicarbonate and then extracted with ethyl acetate, decanted, washed with water until neutral, and dried over sodium sulfate. After filtration and evaporation of the solvent, 130 g (yield 95%) of a product of the following formula are recovered:

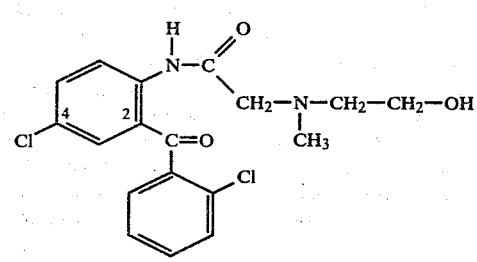

Empirical formula: $C_{18}H_{18}Cl_2N_2O_3$
Molecular weight: 381.26
White crystals
Melting point: 119°–120° C.
Plate chromatography:
support: silica gel 60 F 254 Merck
solvent: ethyl acetate
development: UV and iodine
Rf: 0.73

EXAMPLE 2

N,N'-dimethyl-N-(2-hydroxyethyl)-2'-(ortho-chlorobenzoyl)-4'-chloroglycylanilide (a) Preparation of N-methyl-2'-(ortho-chlorobenzoyl)-4'-chloro-2-bromoacetanilide To a solution of 56 g of 2-methylamino-2',5'-dichlorobenzophenone in 400 cc of ethyl acetate there are added an equal volume of ice and then 23 cc of bromoacetylbromide. After stirring overnight at room temperature, 300 cc of ethyl ether are added. The solvent layer is decanted, washed with 2 N caustic soda, and then washed with water until neutral. It is then dried over sodium sulfate, filtered, and evaporated to dryness. The residue is treated with petroleum ether and then recrystallized from ethyl acetate. In this way there are obtained 65 g of crystals; yield: 81%.

Melting point: 86° C.
Plate chromatography:
support: Silica gel 60 F 254 Merck
solvent: ethyl acetate/petroleum ether 30/70
development: UV and iodine
Rf: 0.33

(b) Preparation of N,N'-dimethyl-N-(2-hydroxyethyl)-2'-(ortho-chlorobenzoyl)-4'-chloroglycylanilide To a solution of 60.15 g (0.15 mol) of N-methyl-2'-(ortho-chlorobenzoyl)-4'-chloro-2-bromoacetanilide in 500 cc of acetone there are added 25 cc (0.31 mol) of 2-methylaminoethanol, followed by heating for 2 hours under reflux. The solution is evaporated to dryness. The residue is dissolved in 1 N hydrochloric acid and washed with ether. The acid aqueous phase is treated with sodium bicarbonate, whereupon it is extracted with ether and washed with water until neutral. It is dried over sodium sulfate and filtered, and the organic phase evaporated. The residue obtained is recrystallized from hexane/ethyl acetate. There is thus recovered, in a yield of 80%, the product of the formula:

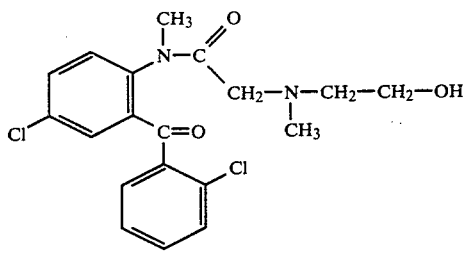

Empirical formula: $C_{19}H_{20}Cl_2N_2O_3$
Molecular weight: 395.27
Crystals: off white
Melting point: 79° C.
Plate chromatography:
support: silica gel 60 F 254 Merck
solvent: butanol/acetic acid/water 6/2/2
development: UV and iodine
Rf: 0.41

EXAMPLE 3 (Compound F 1933)

N,N-bis-(2-hydroxyethyl)-N'-methyl-2'-(ortho-chlorobenzoyl)-4'-chloroglycylanilide hydrochloride To a solution of 40.1 g (01. mol) of N-methyl-2'-(ortho-chlorobenzoyl)-4'-chloro-2-bromoacetanilide in 300 cc of acetone there are added 20 cc (0.2 mol) of diethanolamine, followed by agitation for 24 hours at room temperature. The reaction solvent is evaporated to dryness, the residue treated with a bicarbonate solution and extracted with ethyl acetate. The organic phase is washed three times with water and dried over sodium sulfate. After filtration and evaporation there are recovered 43 g of an oil which is treated with a saturated ethanolic solution of hydrochloric acid; it is precipitated with ethyl ether and iced. After filtration and drying, 32 g of crystals are recovered. Yield: 70% of product of the formula:

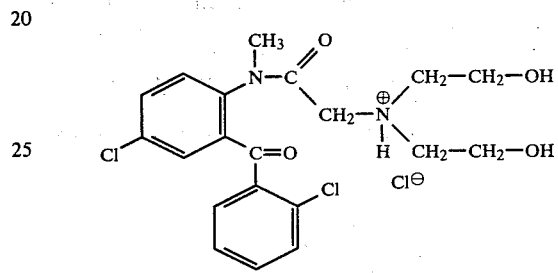

Empirical formula: $C_{20}H_{23}Cl_3N_2O_4$
Molecular weight: 461.77
White crystals
Melting point: 187°–188° C.
Plate chromatography:
support: silica gel 60 F 254 Merck
solvent: butanol/acetic acid/water 6/2/2
development: UV and iodine
Rf: 0.35

EXAMPLE 4

N-(1,1-dimethylpropargyl)-N'-methyl-2'-(ortho-chlorobenzoyl)-4'-chloroglycylanilide hydrochloride To a solution of 7.37 g (0.09 mol) of 1,1-dimethylpropargyl amine in 30 cc of acetone there are added 4.01 g of N-methyl-2'-(ortho-chlorobenzoyl)-4'-chloro-2-bromoacetanilide. After 5 hours at room temperature, the acetone is evaporated, the residue treated with a bicarbonate solution and extraction effected with ethyl acetate. After the customary treatments, as in the preceding Examples, the residual oil is treated with a saturated ethanolic solution of hydrochloric acid. There are recovered, in a yield of 75%, 3.29 g of crystals of the formula:

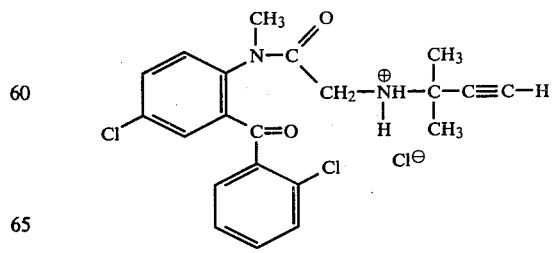

Empirical formula: $C_{21}H_{21}Cl_3N_2O_2$

Molecular weight: 439.77
White crystals
Melting point: 176° C.
Plate chromatography:
support: silica gel 60 F 254 Merck
solvent: butanol/acetic acid/water 6/2/2
development: UV and iodine
Rf: 0.62

EXAMPLE 5 (COMPOUND F 1935)

N-cyclopropyl-N'-methyl-2'-(ortho-chlorobenzoyl)-4'-chloroglycylanilide hydrochloride To a solution of 3.15 g (0.0078 mol) of N-methyl-2'-(ortho-chlorobenzoyl)-4'-chloro-2-bromoacetanilide in 25 cc of methylene chloride there are added 1.6 cc (0.0231 mol) of cyclopropylamine. Agitation is effected for four hours at room temperature; the solvent is evaporated and the residue is treated with a bicarbonate solution. Extraction is effected with ethyl acetate followed by decantation, washing with water and drying over sulfate. After filtration and evaporation, the residual oil obtained is treated with a saturated ethanolic solution of hydrochloric acid. In this way there is recovered, with a yield of 85%, a product of the formula:

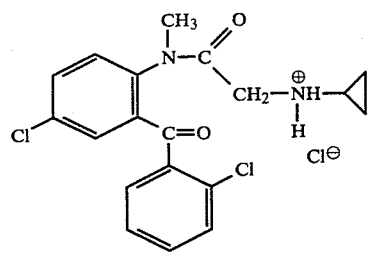

Empirical formula: $C_{19}H_{19}Cl_3N_2O_2$
Molecular weight: 413.73
White crystals
Melting point: 201° C.
Plate chromatography:
support: silica gel 60 F 254 Merck
solvent: butanol/acetic acid/water 6/2/2
development: UV and iodine
Rf: 0.53
Solubility: 0.3% soluble in water.

EXAMPLE 6

N-cyclopentyl-N'-methyl-2'-(ortho-chlorobenzoyl)-4'-chloro-glycylanilide hydrochloride In the manner described in Example 5, but using cyclopentylamine, there is obtained the product of the formula:

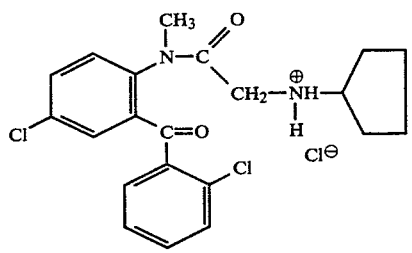

Empirical formula: $C_{21}H_{23}Cl_3N_2O_2$

Molecular weight: 441.79
White crystals
Melting point: 210° C.
Plate chromatography:
support: silica gel 60 F 254 Merck
solvent: methanol/chloroform 50/50
development: UV and iodine
Rf: 0.78
Solubility: 0.5% soluble in water.

EXAMPLE 7

N-cyclohexyl-2'-(ortho-chlorobenzoyl)-4'-glycylanilide hydrochloride

In the manner described in Example 1, but using cyclohexylamine, there is obtained the product of the formula:

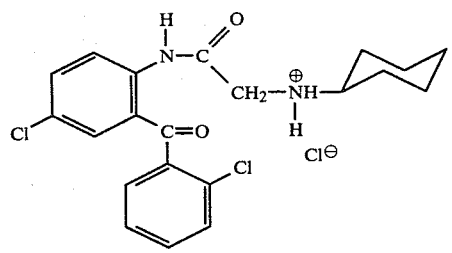

Empirical formula: $C_{21}H_{22}Cl_2N_2O_2$
Molecular weight: 405.33
White crystals
Melting point: 115° C.
Plate chromatography:
support: silica gel 60 F 254 Merck
solvent: ethyl acetate/petroleum ether 30/70
development: UV and iodine
Rf: 0.44
Solubility: 10% soluble in DMSO, methyl pyrrolidone, ethyl acetate, DMA and chloroform.

EXAMPLE 8

N-cyclohexyl-N'-methyl-2'-(ortho-chlorobenzoyl)-4'-chloroglycylanilide acid maleate In the manner described in Example 5, but using cyclohexylamine as amine and maleic acid as salifying agent, there is obtained a product of the formula:

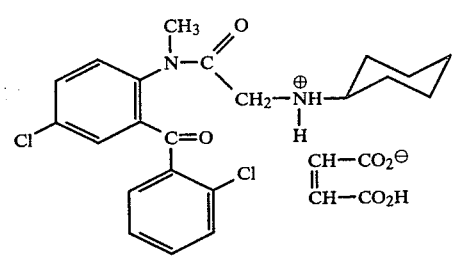

Empirical formula: $C_{26}H_{28}Cl_2N_2O_6$
Molecular weight: 535.43
White crystals
Melting point: 150° C.
Plate chromatography:
support: silica gel 60 F 254 Merck
solvent: butanol/acetic acid/water 6/2/2
development: UV and iodine
Rf: 0.63

Solubility: 1% soluble in propylene glycol.
Insoluble in water. 10% soluble in DMA.

EXAMPLE 9 (COMPOUND F 1939)

N-cyclohexyl-N,N'-dimethyl-2'-(ortho-chlorobenzoyl)-4'-chloroglycylanilide acid maleate In the manner described in Example 5, but using N-methylcyclohexylamine as amine and maleic acid as salifying agent, there is obtained the product of the formula:

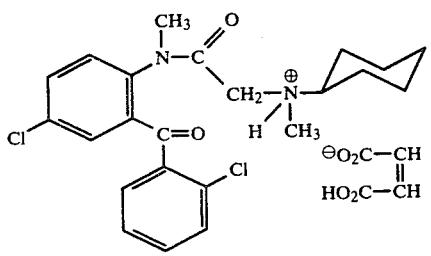

Empirical formula: $C_{27}H_{30}Cl_2N_2O_6$
Molecular weight: 549.45
White crystals
Melting point: 192° C.
Plate chromatography:
support: silica gel 60 F 254 Merck
solvent: butanol/acetic acid/water 6/2/2
development: UV and iodine
Rf: 0.41
Solubility: Insoluble in water. 5% soluble in DMSO.

EXAMPLE 10 (COMPOUND F 1940)

N-methyl-2'-(ortho-chlorobenzoyl)-4'-chloro-2-morpholinoacetanilide acid maleate In the manner described in Example 5, but using morpholine as amine and maleic acid as salifying agent, there is obtained the product of the formula:

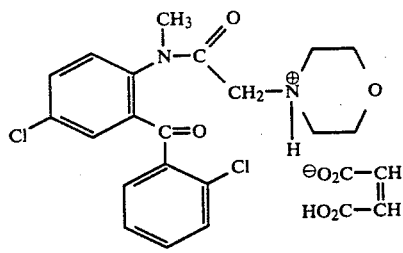

Empirical formula: $C_{24}H_{24}Cl_2N_2O_7$
Molecular weight: 523.37
White crystals
Melting point: 125° C.
Plate chromatography:
support: silica gel 60 F 254 Merck
solvent: butanol/acetic acid/water 6/2/2
development: UV and iodine
Rf: 0.50
Solubility: 1% soluble in water.

EXAMPLE 11

N-methyl-N'-(2-methylallyl)-2'-(ortho-chlorobenzoyl)-4'-chloroglycylanilide

In the manner described in Example 5, but using methyl allylamine, there is obtained a product of the formula:

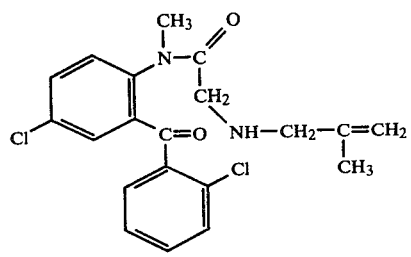

Empirical formula: $C_{20}H_{20}Cl_2N_2O_2$
Molecular weight: 391.3
White crystals
Plate chromatography:
support: silica gel 60 F 254 Merck
solvent: butanol/acetic acid/water 6/2/2
development: UV and iodine
Rf: 0.67

EXAMPLE 12

N-cyclohexyl-N,N'-diethyl-2'-(ortho-chlorobenzoyl)-4'-chloroglycylanilide acid maleate and other N,N'-dialkyl variations In the manner described in Example 5, but using N-ethylcyclohexylamine as amine, maleic acid as salifying agent, and N-ethyl-2'-(ortho-chlorobenzoyl)-4'-chloro-2-bromoacetanilide as starting material of Formula II, there is obtained the above-identified product.

Similarly, in the manner described in Example 5, but using N-propylcyclohexylamine as amine, and maleic acid as salifying agent, there is obtained the product N-cyclohexyl-N-propyl-N'-methyl-2'-(ortho-chlorobenzoyl)-4'-chloroglycylanilide acid maleate.

In substantially the same manner as described in Example 5, but using N-methylcyclohexylamine as amine, maleic acid as salifying agent, and N-amyl-2'-(ortho-chlorobenzoyl)-4'-chloro-2-bromoacetanilide for the starting material of Formula II, there is obtained the product N-cyclohexyl-N-methyl-N'-amyl-2'-(ortho-chlorobenzoyl)-4'-chloro-glycylanilide acid maleate.

Similarly, in the manner described in Example 5, but using N-ethylcyclopropylamine, there is obtained the compound N-cyclopropyl-N-ethyl-N'-methyl-2'-(ortho-chlorobenzoyl)-4'-chloro-glycylanilidehydrochloride.

In the same manner as described in Example 5, but using morpholine, as amine, maleic acid as salifying agent, and N-butyl-2'-(ortho-chlorobenzoyl)-4'-chloro-2-bromoacetanilide as starting material of Formula II, there is obtained the product N-butyl-2'-(ortho-chlorobenzoyl)-4'-chloro-2-morpholinoacetanilide acid maleate.

In the same manner, by varying the substituents R and $R_1$ in the starting material of Formula II and in the amine reactant of Formula III, numerous additional variations in the R and $R_1$ alkyl groups are conveniently obtained.

EXAMPLE 13

N-methyl-2'-(ortho-chlorobenzoyl)-4'-chloro-2-(4''-methylpiperazino)acetanilide acid maleate In the manner described in Example 5, but using N-methylpiperazine as amine and maleic acid as salifying agent, the above-identified product is produced.

EXAMPLE 14

N-methyl-2'-(ortho-chlorobenzoyl)-4'-chloro-2-pyrrolidinoacetanilide acid maleate and additional cyclic variations of $R_1$ and $R_2$ In the manner described in Example 5, but using pyrrolidine as amine and maleic acid as salifying agent, the above-identified product is produced.

In the same manner as given in Example 5, but using piperidine as amine and maleic acid as salifying agent, there is obtained the product N-methyl-2'-(ortho-chlorobenzoyl)-4'-chloro-2-piperidino-acetanilide acid maleate.

In the same manner as given in Example 5, but using pyrrolidine as amine, maleic acid as salifying agent, and N-propyl-2'-(ortho-chlorobenzoyl)-4'-chloro-2-bromoacetanilide as starting material of Formula II, there is obtained the product N-propyl-2'-(ortho-chlorobenzoyl)-4'-chloro-2-pyrrolidinoacetanilide acid maleate.

In the same manner as given in Example 5, but using imidazolidine instead of cyclopropylamine, there is obtained the product N-methyl-2'-(ortho-chlorobenzoyl)-4'-chloro-2-imidazolidino-acetanilidehydrochloride.

In exactly the same manner, but substituting pyrazolidine for imidazolidine, there is obtained the product N-methyl-2'-(ortho-chlorobenzoyl)-4'-chloro-2-pyrazolidinoacetanilidehydrochloride.

In exactly the same manner, but substituting pyrrole, imidazole, pyrazole, isoxazole, pyridine, pyrazine, pyrimidine, or pyridazine for the cyclopropylamine of Example 5, the following products are obtained:

N-methyl-2'-(ortho-chlorobenzoyl)-4'-chloro-2-pyrrolinoacetanilide hydrochloride, N-methyl-2'-(ortho-chlorobenzoyl)-4'-chloro-2-imidazolinoacetanilide hydrochloride, N-methyl-2'-(ortho-chlorobenzoyl)-4'-chloro-2-pyrazolinoacetanilide hydrochloride, N-methyl-2'-(ortho-chlorobenzoyl)-4'-chloro-2-isoxazolinoacetanilide hydrochloride, N-methyl-2'-(ortho-chlorobenzoyl)-4'-chloro-2-pyridinoacetanilide hydrochloride, N-methyl-2'-(ortho-chlorobenzoyl)-4'-chloro-2-pyrazinoacetanilide hydrochloride, N-methyl-2'-(ortho-chlorobenzoyl)-4'-chloro-2-pyrimidinoacetanilide hydrochloride, and N-methyl-2'-(ortho-chlorobenzoyl)-4'-chloro-2-pyridazinoacetanilide hydrochloride.

Similarly, by substituting additional heterocyclic amines for the morpholine of Example 10 or the cyclopropylamine of Example 5, additional compounds within the scope of the invention are obtained, having additional cyclic variations of the $R_1$ and $R_2$ substituents.

EXAMPLE 15

N-methylcyclopentyl-N'-methyl-2'-(ortho-chlorobenzoyl)-4'-chloro-glycylanilide hydrochloride In the manner of Example 6, but substituting methylcyclopentylamine for cyclopentylamine, there is obtained the above-identified product.

EXAMPLE 16

N-ethylcyclopentyl-N'-methyl-2'-(ortho-chlorobenzoyl)-4'-chloro-glycylanilide hydrochloride In the manner of Example 6, but substituting ethylcyclopentylamine for the cyclopentylamine of Example 6, there is obtained the above-identified product.

EXAMPLE 17

N-ethylcyclohexyl-N'-methyl-2'-(ortho-chlorobenzoyl)-4'-chloro-glycylanilide hydrochloride In the same manner as given in Example 6, but using ethylcyclohexylamine instead of the cyclopentylamine there employed, there is obtained the above-identified product.

EXAMPLE 18

N-cyclohexyl-N,N'-diamyl-2'-(ortho-chlorobenzoyl)-4'-chloro-glycylanilide acid maleate In the same manner as given in Example 5, but using N-amylcyclohexylamine as amine, maleic acid as salifying agent, and N-amyl-2'-(ortho-chlorobenzoyl)-4'-chloro-2-bromoacetanilide as starting material of Formula II, there is obtained the above-identified product.

EXAMPLE 19

N-methyl-2'-(ortho-chlorobenzoyl)-4'-chloro-2-ethylmorpholinoacetanilide acid maleate In the manner of Example 5, but using ethylmorpholine as amine and maleic acid as salifying agent, there is obtained the above-identified product.

EXAMPLE 20

N-propyl-2'-(ortho-chlorobenzoyl)-4'-chloro-2-methylmorpholinoacetanilide acid maleate In the manner of Example 5, but using methylmorpholine as amine, maleic acid as salifying agent, and N-propyl-2'-(ortho-chlorobenzoyl)-4'-chloro-2-bromoacetanilide as starting material of Formula II, there is obtained the above-identified product.

PHARMACOLOGY AND TOXICOLOGY

The compounds of the present invention, which exert remarkable activity on the central nervous system, can therefore be administered to man or to animal orally or by injection in the form of a free base or else in the form of a therapeutically acceptable salt. The new derivatives obtained in the foregoing manner, which are bases, can be converted into addition salts with acids, which form part of the invention. The addition salts can be obtained by the reaction of the new derivatives with acids in suitable solvents such, for example, as shown by the examples. As acids used for the formation of these addition salts there may be mentioned, in the mineral series: hydrochloric, hydrobromic, methanesulphonic, sulphuric and phosphoric acid; in the organic series: acetic, propionic, maleic, fumaric, tartaric, citric, oxalic, benzoic acid, to name a few. The invention accordingly also relates to the salts with organic or inorganic acids, especially lipophilic acids, e.g., fatty acids having 14 to 22 carbon atoms, inclusive, which are linear or branched, saturated or unsaturated, including palmitic, linoleic, linolenic, and oleic acids, and the like, as well as of the naphthoic type, especially pamoic acid, in addition to the usual organic and inorganic acids of the type already mentioned. The selection of the free base or acid addition salt thereof and preparation of the desired acid addition salt of a compound in any particular case will be apparent and fully within the ability of one skilled in the art. The novel compounds are frequently used in the form of their pharmaceutically acceptable acid addition salts, e.g., their hydrochlorides, hydrobromides, or the like. The salt is usually the best form for pharmaceutical formulations. Innumerable other pharmaceutically-acceptable acid addition salts can be prepared from the hydrochlorides via the free bases in conventional manner.

By way of simple illustration, there will be set forth below a few results of the various toxicological and pharmacological tests carried out on the compounds of the invention.

(a) Toxicity study

The compounds of the present invention were subjected to toxicity verifications. The toxicity of certain compounds, determined by the fifty percent lethal dose, is set forth in the following table. It was determined on lots of ten mice by oral administration and calculated by the method of MILLER and TAINTER (Proc. Soc. Exper. Biol. Med., 1944, 57, 261).

(b) Activity in the Rota Rod test

This test is carried out on male mice of Swiss strain.

The mice are placed on a wooden rod of a diameter of three cm, rotating at the rate of five rpm. The mice which can remain on the rod for at least three minutes during successive tests are selected and collected in groups of ten for the test of each dose.

If the mouse falls from the rod in less than two minutes, the compound tested is considered effective.

The results are expressed in $ED_{50}$ in accordance with N. W. DUNHAM and T. S. MIVA (J. Amer. Pharm. Asso., 1957, 46, 208).

(c) Antagonistic activity to pentetrazol

This test is carried out on a group of ten male mice of Swiss strain. Within fifteen minutes after subcutaneous injection of 125 mg/kg of pentetrazol, the mice have tonic convulsions resulting in death. For the test, the compounds are administered orally sixty minutes before the injection of pentetrazol. The animals are observed for two hours after administration of the pentetrazol.

The results are expressed by the $ED_{50}$ dose in accordance with GOODMANN et al. (J. Pharmacol. 108, 1953).

TABLE OF RESULTS

| Y | TOXICITY per os $DE_{50}$ mg/kg | ROTA ROD per os $DE_{50}$ mg/kg | PENTE-TRAZOL per os $DE_{50}$ mg/kg |
|---|---|---|---|
| $-N(CH_3)-CH_2-CH_2OH$ | 750 | 17 | 0.9 |
| $-N(CH_2-CH_2OH)_2$ | ≈1000 | 15 | 0.5 |
| $-N(H)-C(CH_3)_2-C{\equiv}C-H$ | 420 | 19 | 1 |
| $-NH$-cyclopropyl | >1000 | 7 | 0.3 |
| $-NH$-cyclobutyl | 750 | 16 | 1.9 |
| $-NH$-cyclohexyl | >1000 | 20 | 0.7 |
| $-N(CH_3)$-cyclohexyl | >1000 | 21 | 0.8 |
| morpholino | >1000 | 20 | 0.8 |
| $-N(H)-CH_2-C(CH_3)=CH_2$ | >1000 | 10 | 0.4 |

On a basis of their pharmacological properties and their low toxicity, these chemical compounds can be used in therapy for the treatment of anxiety and neuroses.

These compounds and their therapeutically acceptable acid addition salts can be used as medicaments, for instance, in the form of pharmaceutical preparations adapted for oral or parenteral administration in admixture with, for instance, water, lactose, gelatin, starches, magnesium stearate, talc, vegetable oils, gums, polyalkylene glycols, vaseline, etc. These preparations may be in solid form, for instance, in the form of tablets, pills, capsules, etc., or in liquid form, for example, solutions, suspensions or emulsions.

Pharmaceutical preparations in a form suitable for injection are preferred. These preparations may be subjected to conventional pharmaceutical operations such as sterilization and/or may contain adjuvants, for example, preservatives, stabilizers, wetting or emulsifying agents, buffering compounds, etc.

The doses in which the active compounds and their therapeutically compatible acid addition salts can be administered can vary with wide ranges depending on the size, weight, and condition of the patient. A daily dose of about 0.01 mg to 1 mg/kg of body weight is, however, preferred.

The pharmaceutical compositions of the invention can be used in internal medicine, as anxiolytic agents, i.e., for the treatment of anxiety states of whatever origin, for instance in the treatment of organic pathological conditions such as arterial hypertension and coronaritis, accompanied and aggravated by a state of anxiety or in psychosomatic medicine, for instance for the treatment of asthma, gastro-duodenal ulcers, colonopathy and other functional digestive ailments, accompanied by or resulting from anxiety, as well as in psychiatry, for instance for treatment of anxiety conditions of agitation in psychotic subjects.

For these various purposes, the compounds of the invention are, of course, administered in doses which vary with their nature, with the method of administration, and with the treatment desired.

Pharmaceutical preparations containing these active principles may be administered orally, parenterally, rectally and locally, in each case for their intended purpose.

For oral administration tablets, capsules and elixirs may be used, the unit dose being 5 to 500 mg, in accordance with a usual maximum daily dose in man of 500 mg. For rectal administration these quantities are usually 100 to 500 mg respectively.

The pharmaceutical compositions may also contain other pharmaceutically and therapeutically compatible active principles.

A few examples of pharmaceutical preparations which contain a representative active principle forming an object of the invention are given below, by way of illustration only and not by way of limitation:

(a) tablets F 1933, 1935, 1939 or 1940 150 mg+excipient (b) suppository, adult, strong: F 1933, 1935, 1939 or 1940 200 mg+suppository excipient (c) capsules: F 1933, 1935, 1939 or 1940 75 mg plus excipient 100 mg; or F 1933, 1935, 1939 or 1940 alone.

For oral use, the compounds are usually administered as tablets, solutions, suspensions, or the like, in which they are present together with usual pharmaceutical carriers, excipients, binders, and the like. For example, tablets may be prepared conventionally by compounding one of the new compounds with customary carriers and adjuvants, e.g., talc, magnesium stearate, starch, lactose, gelatin, gums and the like. In their most advantageous form, then, the compositions of the present invention will contain a non-toxic pharmaceutical carrier in addition to the active ingredient. Exemplary carriers are: Solids: lactose, magnesium stearate, calcium stearate, starch, terra alba, dicalcium phosphate, sucrose, talc, stearic acid, gelatin, agar, pectin, acacia, or other usual excipient; Liquids: peanut oil, sesame oil, olive oil, water, elixir, or other usual excipient. The active agents of the invention can usually be most conveniently administered in such compositions containing about 0.01 to 67 percent, preferably 0.04 to 12.15 percent, by weight of the active ingredient. Such formulations are representatively illustrated in U.S. Pat. No. 3,402,244.

A wide variety of pharmaceutical forms suitable for many modes of administration and dosages may be employed. For oral administration, the active ingredient and pharmaceutical carrier may, for example, take the form of a granule, pill, tablet, lozenge, elixir, syrup, or other liquid suspension or emulsion; and for rectal administration, a suppository. For topical or dermatological use and administration, an ointment, salve, solution, or suspension of usual type may be employed.

The method of using the compounds of the present invention comprises administering a compound of the invention, preferably admixed with a pharmaceutical carrier, for example, in the form of any of the above-mentioned compositions, or filled into a capsule, to alleviate one or more of the foregoing enumerated abnormal conditions and symptoms, especially anxiety, in a living animal body, whether human or domestic animal, for example, the afore-mentioned anxiety types. The compounds are subject to usual variations in optimum daily and unit dosages, due to patient body weight, condition, and ancillary factors, and the invention therefore should not be limited by the exact ranges stated. The exact dosage, both unit and daily, will of course as usual have to be determined according to established veterinary and medical principles.

It is to be understood that the invention is not to be limited to the exact details of operation or exact compounds, compositions, or procedures shown and described, as obvious modifications and equivalents will be apparent to one skilled in the art, and the invention is therefore to be limited only by the scope of the appended claims.

We claim:

1. 2'-(ortho-chlorobenzoyl)-4'-chloroglycylanilides selected from compounds having the formula I:

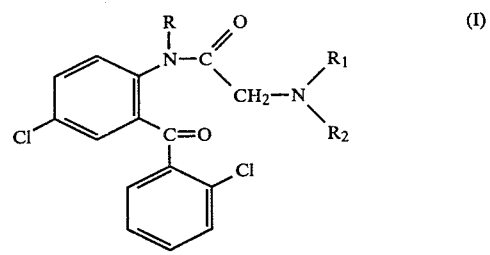

in which:
R represents hydrogen or lower-alkyl;
$R_1$ and $R_2$ are lower-hydroxyalkyl,
and pharmaceutically acceptable inorganic or organic acid addition salts thereof.

2. A compound of claim 1 which is N,N-bis-(2-hydroxyethyl)-N'-methyl-2'-(ortho-chlorobenzoyl)-4'-chloroglycylanilide or a pharmaceutically-acceptable acid addition salt thereof.

3. A compound of claim 1 which is N,N-bis-(2-hydroxyethyl)-N'-methyl-2'-(ortho-chlorobenzoyl)-4'-chloroglycylanilide hydrochloride.

* * * * *

UNITED STATES PATENT AND TRADEMARK OFFICE
CERTIFICATE OF CORRECTION

PATENT NO. : 4,380,667
DATED : April 19, 1983
INVENTOR(S) : Gilbert Mouzin, Henri Cousse and Antoine Stenger It is certified that error appears in the above—identified patent and that said Letters Patent is hereby corrected as shown below:

Title Page, [57] ABSTRACT, 5th line from bottom; "lower alkyl" should read -- lower-alkyl --
Col. 3, approximately line 33 (last formula);

" 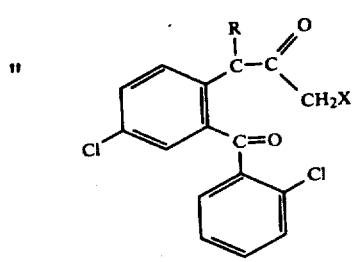     should read     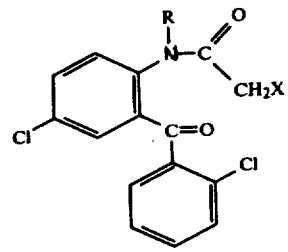 --

Col. 6, line 5; "(01. mol)" should read -- (0.1 mol) --
Col. 15, line 11; "with" should read -- within --

Signed and Sealed this

Second Day of August 1983

[SEAL]

Attest:

GERALD J. MOSSINGHOFF

Attesting Officer

Commissioner of Patents and Trademarks